US005736333A

United States Patent [19]
Livak et al.

[11] Patent Number: 5,736,333
[45] Date of Patent: Apr. 7, 1998

[54] PASSIVE INTERNAL REFERENCES FOR THE DETECTION OF NUCLEIC ACID AMPLIFICATION PRODUCTS

[75] Inventors: Kenneth J. Livak, San Jose; Lincoln J. McBride, Belmont, both of Calif.

[73] Assignee: The Perkin-Elmer Corporation, Foster City, Calif.

[21] Appl. No.: 657,989

[22] Filed: Jun. 4, 1996

[51] Int. Cl.$^6$ ............... C12Q 1/68; C12P 19/34; C07H 21/04
[52] U.S. Cl. ............... 435/6; 435/91.2; 536/23.1
[58] Field of Search ............... 435/6, 91.2, 810; 536/23.1

[56] References Cited

U.S. PATENT DOCUMENTS

| | | | |
|---|---|---|---|
| 5,210,015 | 5/1993 | Gelfand et al. | 435/6 |
| 5,527,684 | 6/1996 | Mabile et al. | 435/7.1 |

OTHER PUBLICATIONS

Lee et al., Nucleic Acids Res. 21(16), 3761–3766 (1993).
Holland et al., Proc. Natl. Acad. Sci. USA 88, 7276–7280 (1991).
Livak et al., PCR Meth. Applic. 4, 357–362 (Jun. 1995).
Higuchi et al., Biotechnology 10, 413–417 (1992).

*Primary Examiner*—Kenneth R. Horlick
*Attorney, Agent, or Firm*—Scott R. Bortner; The Perkin-Elmer Corporation

[57] ABSTRACT

The invention relates to passive internal references for use in quantitating the formation of amplification products in a nucleic amplification reaction. The internal amplification reference molecules of the invention comprise a first and second fluorophore joined together through a backbone connector. The first and second fluorophores are joined on the backbone in a configuration that permits the energy transfer from the first fluorophore to the second fluorophore. The backbone connector is selected so as not to bind to the target nucleic acid sequence under nucleic acid amplification conditions. Preferably, the backbone connector is a polynucleotide. Another aspect of the invention is to provide passive internal reference molecule containing reagent compositions for use in nucleic acid amplification reactions. The compositions comprise the internal amplification reference molecule of the invention and a nucleic acid amplification reaction buffer. The reagent compositions, optionally, include additional components required for nucleic acid amplification reactions. The invention also provides improved methods of measuring the amount of amplification product in nucleic acid amplification reactions employing fluorescer-quencher probe assays, including methods for the real-time measurement of amplification product formation. The methods comprise the step of adding the internal reference molecule of the invention to the amplification reaction mixture. Fluorescence of the second fluorophore on the internal reference may then be measured and used to calculate changes in fluorescence of the fluorophore on a fluorescer-quencher probe.

21 Claims, 6 Drawing Sheets

PASSIVE INTERNAL REFERENCES FOR THE DETECTION OF NUCLEIC ACID AMPLIFICATION PRODUCTS

The invention relates generally to the field of nucleic acid amplification, and more particularly to a system for measuring in real time polynucleotide products from nucleic acid amplification processes, such as polymerase chain reaction (PCR).

BACKGROUND

Nucleic acid sequence analysis is becoming increasingly important in many research, medical, and industrial fields, e.g. Caskey, Science 236: 1223–1228 (1987); Landegren et al, Science, 242: 229–237 (1988); and Arnheim et al, Ann. Rev. Biochem., 61: 131–156 (1992). The development of several nucleic acid amplification schemes has played a critical role in this trend, e.g. polymerase chain reaction (PCR), Innis et at, editors, PCR Protocols (Academic Press, New York, 1990); McPherson et at, editors, PCR: A Practical Approach (IRL Press, Oxford, 1991); ligation-based amplification techniques, Barany, PCR Methods and Applications 1: 5–16 (1991); and the like.

PCR in particular has become a research tool of major importance with applications in cloning, analysis of genetic expression, DNA sequencing, genetic mapping, drug discovery, and the like, e.g. Arnheim et al (cited above); Gilliland et al, Proc. Natl. Acad. Sci., 87: 2725–2729 (1990); Bevan et at, PCR Methods and Applications, 1: 222–228 (1992); Green et al, PCR Methods and Applications, 1: 77–90 (1991); Blackwell et at, Science, 250: 1104–1110 (1990).

A wide variety of instrumentation has been developed for carrying out nucleic acid amplifications, particularly PCR, e.g. Johnson et at, U.S. Pat. No. 5,038,852 (computer-controlled thermal cycler); Wittwer et at, Nucleic Acids Research, 17: 4353–4357 (1989)(capillary tube PCR); Hallsby, U.S. Pat. No. 5,187,084 (air-based temperature control); Garner et al, Biotechniques, 14: 112–115 (1993) (high-throughput PCR in 864-well plates); Wilding et at, International application No. PCT/US93/04039 (PCR in micro-machined structures); Schnipelsky et al, European patent application No. 90301061.9 (publ. No. 0381501 A2)(disposable, single use PCR device), and the like. Important design goals fundamental to PCR instrument development have included fine temperature control, minimization of sample-to-sample variability in multi-sample thermal cycling, automation of pre- and post-PCR processing steps, high speed cycling, minimization of sample volumes, real time measurement of amplification products, minimization of cross-contamination, or sample carryover, and the like. In particular, the design of instruments that permit PCR to be carded out in closed reaction chambers and monitored in real time is highly desirable. Closed reaction chambers are desirable for preventing cross-contamination, e.g. Higuchi et at, Biotechnology, 10: 413–417 (1992) and 11: 1026–1030 (1993); and Holland et al, Proc. Natl. Acad. Sci., 88: 7276–7280 (1991). Clearly, the successful realization of such a design goal would be especially desirable in the analysis of diagnostic samples, where a high frequency of false positives and false negatives would severely reduce the value of the PCR-based procedure. Real time monitoring of a PCR permits far more accurate quantitation of starting target DNA concentrations in multiple-target amplifications, as the relative values of close concentrations can be resolved by taking into account the history of the relative concentration values during the PCR. Real time monitoring also permits the efficiency of the PCR to be evaluated, which can indicate whether PCR inhibitors are present in a sample.

Holland et al (cited above) and others have proposed fluorescence-based approaches to provide real time measurements of amplification products during a PCR. Such approaches have either employed intercalating dyes (such as ethidium bromide) to indicate the amount of double stranded DNA present (Higuchi et al, Biotechnology 10:413–417 (1992), Higuchi et al, Biotechnology 11:1026–1030 (1993), U.S. Pat. No. 5,210,015) or they have employed probes containing fluorescer-quencher pairs that are cleaved during amplification to release a fluorescent product whose concentration is proportional to the amount of double stranded DNA present. An example of such a system is the Taqman™ LS-50 PCR Detection system (Perkin-Elmer). Fluorescer-quencher probe assays involve the measurement of the ratio of the fluorescence of the reporter,. i.e, the fluorescer, divided by the fluorescence of the quencher. Fluorescer-quencher probes are polynucleotides labeled with two (or more) different fluorescent indicators. The first fluorescent indicator, upon excitation, serves to excite the quencher, rather than produce an detectable fluorescence emission. The fluorescer-quencher probe hybridizes to a polynucleotide sequence for amplification in PCR or similar amplification reactions. The 5'-3' exonuclease activity of the enzyme used to catalyze the amplification reaction serves to cleave the polynucleotide probe, thereby removing the quencher from its close proximity to the fluorescer so that the signal from the fluorescer is no longer quenched. Detailed descriptions of nucleic acid amplification reactions employing fluorescer-quencher probes can be found in many publications, including Lee et al, Nucleic Acid Research, 21: 3761–3766 (1993), Livak et al, PCR Methods and Applications, 4:357–362 (1995).

It is of interest to perform fluorescer-quencher probe assays with an internal fluorescensce reference so as to provide for accurate and precise measurements of changes in fluorescence levels that are attributable to formation of the amplification products. The development of suitable internal references for such assays has proven to be difficult, particularly for real-time assays because of fluctuations in the signal from the reference. Analysis of the results of a fluorescer-quencher probe assay is complicated beacause the quantum yield of the the fluorescer increases after cleavage and the quantum yield of the quencher decreases. Accordingly, measurements of the fluorescence of the quencher will decrease with amplification rather than providing a relatively constant base-line measurement. An additional fluorescent dye can be added to serve as internal reference. The restrictions on this internal reference include that it not interfere with the amplification process, that it generate a stable fluorescent signal throughout the thermal regimen of amplification, and that its fluorescence emmision be distinguishable from all the fluorescers and quenchers used in the fluorescer-quencher probes. This last restriction generally means that compounds that could be used as internal references are not excited very efficiently at the wavelength used to excite the fluorescers in probes. This problem can be overcome by increasing the concentration of internal reference dye, but the high levels of fluorescent compound required may have adverse effects on the amplification process. Also, high concentrations of internal reference dye can mask the signal from fluorescers by inter-filter effect. Furthermore, many fluorophores are not highly soluble in aqueous solutions.

In view of these problems with conventional internal references for the detection of nucleic acid amplication products, it is of interest to develop new internal references and improved amplification methods employing such standards. The invention described herein provides for such internal references and methods.

SUMMARY OF THE INVENTION

The invention relates to passive internal references for use in quantitating the formation of amplification products in a nucleic amplification reaction. The internal amplification reference molecules of the invention comprise a first and second fluorophore joined together through a backbone connector. The first and second fluorophores are joined on the backbone in a configuration that permits the energy transfer from the first fluorophore to the second fluorophore. The backbone connector is selected so as not to bind to the target nucleic acid sequence under nucleic acid amplification conditions. Preferably, the backbone connector is a polynucleotide.

Another aspect of the invention is to provide passive internal reference molecule containing reagent compositions for use in nucleic acid amplification reactions. The compositions comprise the internal amplification reference molecule of the invention and a nucleic acid amplification reaction buffer. The reagent compositions, optionally, include additional components required for nucleic acid amplification reactions.

The invention also provides improved methods of measuring the amount of amplification product in nucleic acid amplification reactions employing fluoresce-quencher probe assays, including methods for the real-time measurement of amplification product formation. The methods comprise the step of adding the internal reference molecule of the invention to the amplification reaction mixture. Fluorescence of the second fluorophore on the internal reference may then be measured and used to calculate changes in fluorescence of the fluorophore on a fluorescer-quencher probe. The use of the internal reference of the invention permits the simultaneous use of multiple fluorescer-quencher probes in fluorescer-quencher probe assays.

The invention also relates to a system for carrying out real time fluorescence-based measurements of nucleic acid amplification products. In a preferred embodiment of the invention, an excitation beam is focused into a reaction mixture containing (i) a fluorescent indicator capable of generating a first fluorescent signal whose intensity is proportional to the mount of an amplification product in the volume of the reaction mixture illuminated by the excitation beam and (ii) a fluorophore present on an internal amplification reference molecule, i.e., the second fluorophore, homogeneously distributed throughout the reaction mixture and capable of generating a second fluorescent signal proportional to the volume of reaction mixture illuminated by the excitation beam. It is understood that the proportionality of the fluorescent intensities is for a constant set of parameters such as temperature, pH, salt concentration, and the like, that independently influence the fluorescent emissions of organic dyes.

Preferably, the excitation beam is focused into the reaction mixture by a lens through a portion of a wall of a closed reaction chamber containing the reaction mixture. In further preference, the same lens collects the fluorescent signals generated by the fluorescer on a probe and the second fluorophore of the internal reference, in response to the excitation beam; thus, variability in the collected signal due to misalignment of excitation and collection optics is avoided. In this embodiment, whenever the lens directs the excitation beam through a portion of a wall of the closed reaction chamber which is not in contact with the reaction mixture, that portion of the wall is heated so that condensation from the reaction mixture does not form in the optical pathway of the fluorescent signals being collected by the lens, thereby removing another source of variability in the collected signal.

In the most preferred embodiment of the apparatus, the reaction chamber is a tube with a closed end, referred to herein as the bottom of the tube, and an open end, referred to herein as the top of the tube, which can be closed with a cap such that a leak-proof seal is formed. In other words, once a reaction mixture is placed in the tube and the cap is attached a closed reaction chamber is formed. In this most preferred embodiment, (1) the reaction mixture fills a portion of the tube, generally at the bottom of the tube, such that a void is left between the cap of the tube and a top surface of the reaction mixture, and (2) the lens without contacting the cap focuses the excitation beam through the cap into the reaction mixture through its top surface and collects the resulting fluorescence generated by the probes and the internal reference. As mentioned above, the portion of the tube through which the excitation beam passes—the cap in this embodiment—is heated to prevent the formation of condensation which would introduce an added source of variability in the measurement of the collected fluorescent signals. Potential variability that could arise from sequential analysis of the first and second fluorescent signals is eliminated by simultaneously analyzing the signals by spectrally separating the signal light onto an array of photo detectors, e.g. by diffracting the signal onto a charged-coupled device (CCD) array.

As discussed more fully below, an excitation beam generated by a single light source, e.g. a laser, is conveniently distributed to a plurality of closed reaction chambers by fiber optics. Likewise, the same fiber optics can collect the fluorescent signals from the plurality of reaction chambers for analysis by a single detection and analysis system.

Preferably, the system is employed with the PCR amplification of nucleic acids.

The system of the invention permits accurate real time monitoring of nucleic amplification reactions by providing apparatus and fluorescent reagents for generating a stable fluorescent signal proportional to the amount of amplification product and independent of variations in the volume of reaction mixture. The availability of data showing the progress of amplification reactions leads to more accurate estimates of relative starting concentrations of target nucleic acids, to rapid assessment of the efficiency of the amplification reactions, and opens the possibility of reduced reagent usage and feedback reaction control.

DEFINITIONS

Figure 1:
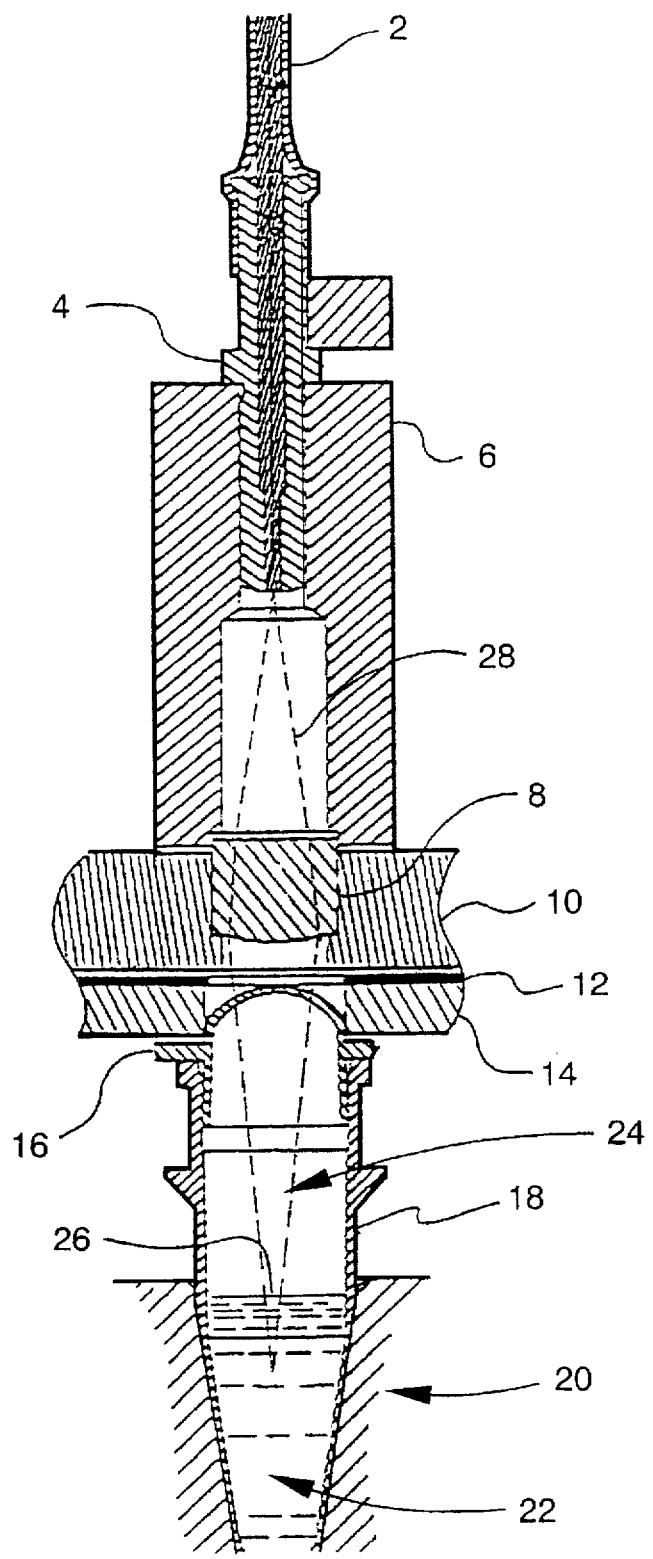
FIG. 1 diagrammatically illustrates a preferred embodiment of the sample interface components of the system of the invention.

As used herein, the term "stable" in reference to a fluorescent signal means that the root means square (RMS) deviation in the signal due to noise is less than or equal to two percent of the average signal magnitude. More preferably, stable means that the RMS deviation in the signal due to noise is less than or equal to one percent of the average signal magnitude.

DETAILED DESCRIPTION OF THE INVENTION

The invention relates to fluorescence-based systems for monitoring in real time the progress of a nucleic acid amplification reaction; however, such systems may also be used for end point measurements. Specifically, the invention relates to passive internal reference molecules that can be used to improve the accuracy and precision of the real time monitoring of nucleic acid amplification reactions. The subject reference molecules are "passive" in that the fluorescence of the reference molecule does not significantly change during a nucleic acid amplification reaction. The use of the internal reference molecules of the invention has significant advantages over only measuring the fluorescence of the quencher on the probe in fluorescer-quencher probe assay. One or more of such advantages can be found in selected embodiments of the invention. One such advantage is that the level of the fluorescent signal from the internal reference remains essentially constant throughout a fluorescer-quencher probe assay. Another advantage of the internal references of the invention is that they permit the simultaneous use of multiple fluorescer-quencher probes in a single amplification reaction. Another advantage of the internal amplification reference molecules of the invention is that they permit the use of fluorescer-quencher probes in which the quencher does not need to be a fluorescer, thereby increasing range of fluorescent molecules that can be used as fluorescers.

The internal reference molecules of the invention comprise a first and second fluorophore joined together though a backbone connector so as to permit the transfer of energy from the first fluorophore to the second fluorophore. The backbone is selected so as to not significantly hybridize to the polynucleotide sequence for amplification in a given specific fluorescer-quencher probe assay during a nucleic acid amplification reaction.

The first fluorophore may be any dye with suitable fluorescence properties covalently attached to a backbone connector, such as an oligonucleotide. Examples of fluorophores covalently attached to oligonucleotides can be found, among other places, in the fluorescer-quencher probe approach described by Holland et at, Proc. Natl. Acad. Sci., 88: 7276-7280 (1991) and in international patent application publication number WO 95/21266.

Dyes employed as second fluorophores include fluorescent dyes whose fluorescent characteristics are substantially unaffected by the presence or association with nucleic acids, particularly double stranded DNA. Such dyes may include virtually any fluorescent dye fulfilling this criterion which is also spectrally resolvable from whatever fluorophores that are employed on fluorscer-quencher probes. Dyes suitable as first fluorophores may also be suitable as second fluorophores. Similarly, dyes suitable as second fluorophores may also be suitable as first fluorophores. Preferred second fluorophores include rhodamine dyes and fluorescein dyes. More preferably, the second fluorophore is the latter being disclosed by Menchen et at, U.S. Pat. No. 5,188,934.

In one embodiment of the invenetion, the first and a second fluorophores are both covalently attached to an oligonucleotide, i.e., the backbone connector, as described by Lee et at, Nucleic Acid Research, 21: 3761-3766 (1993). More specifically, fluorescein is used as the first fluorophore and 6-carboxy-X-rhodamine (ROX) is used as the second fluorophore such that the ROX moiety substantially quenches any fluorescent emissions by the fluorescein moiety. Preferably, in this embodiment, an excitation beam is generated from the 488 nm emission line of an argon ion laser. In this embodiment, preferably the first fluorophore is fluorescein, e.g. 6-FAM (available from Applied Biosystems, Foster City), and the second fluorophore is either tetramethylrhodamine, 2',4',5',7',-tetrachloro-4,7-dichlorofluorescein or 6-carboxy-X-rhodamine.

The backbone connector of the internal reference is designed so as to bring the first fluorophore into close proximity with the second fluorophore so as to permit efficient energy transfer from the first fluorophore to the second fluorophore. In designing suitable backbone connectors, it is important to bear in mind that transfer of energy between fluorophores is a function of $1/R^6$, where R is the distance between the fluorophores. Guidance concerning the selection of an appropriate distance for a given embodiment is found in numerous references on resonant energy transfer between fluorescent molecules and quenching molecules (also sometimes referred to as "donor" molecules and "acceptor" molecules, respectively), e.g. Stryer and Haugland, Proc. Natl. Acad. Sci., 58: 719-726 (1967); Clegg, Meth. Enzymol., 211: 353-388 (1992); Cardullo et at, Proc. Natl. Acad. Sci., 85: 8790-8794 (1988); Ozaki et al (cited above); Haugland (cited above); Heller et at, Fed. Proc., 46: 1968 (1987); Livak et al, PCR Methods and Applications, 4:357-362 (1995), and the like. The backbone is usually, although not necessarily, a polymeric chain. Various, backbones may be employed, such as nucleic acids, both RNA and DNA, various synthetic polynucleotide analogs, e.g., wherein oxygens may be substituted by sulfur, carbon, or nitrogen, phosphates, substituted by sulfate or carboxylates, etc., polypeptides, polysaccharides, and the like. The fluorophores may be joined to the backbone by appropriate functionalization of the fluorophores and/or the polymer building blocks. Detailed description of how to join fluorophores to various backbone can be found in, among other places, Bioconjugate Techniques, by G. T. Hermanson, Academic Press, San Diego (1996), European Patent Application publication 0 229 943 (published 1987), and Ju et at, Analytical Biochmeistry, 231:131-140 (1995).

The backbone connector is designed so as not to significantly hybridize in a sequence specific manner to the polynucleotides for amplification in given amplification reaction during the amplification reaction. In some embodiments of the invention, the backbone connector may hybridize to the polynucleotides sequence for amplification, either before or after the amplification process. Generally, this potential problem exists only when the backbone connector is a polynucleotide (or a derivative thereof). If the backbone did specifically hybridize to the sequence for amplification, the backbone might significantly interfere with the ability of a fluorescer-quencher probe to hybridize to the polynucleotide sequence for amplification. Non-hybridizing polynucleotides for use as backbone connectors may readily be obtained by using polynucleotides that lack significant sequence homology to the polynucleotide sequence for amplification.

Internal reference molecules (having polynucleotides as backbones) may be synthesized by a number of approaches, e.g. Ozaki et at, Nucleic Acids Research, 20: 5205–5214 (1992); Agrawal et al, Nucleic Acids Research, 18: 5419–5423 (1990); or the like. Such synthesis methods are also applicable to the synthesis of fluorescer-quencher probes. Preferably, the oligonucleotide probes are synthesized on an automated solid phase DNA synthesizer using phosphoramidite chemistry, e.g. Applied Biosystems, Inc. model 392 or 394 DNA synthesizer (Foster City, Calif.). The first and second fluorophores can be covalently attached to predetermined nucleotide of an oligonucleotide by using nucleoside phosphoramidite monomers containing reactive groups. For example, such reactive groups can be on a phosphate, or phosphate analog, e.g. Agrawal et al (cited above), on the 5' hydroxyl when attachment is to the 5' terminal nucleotide, e.g. Fung et at, U.S. Pat. No. 4,757,141 or Hobbs Jr., U.S. Pat. No. 4,997,928, and on base moieties, e.g. as disclosed by Ruth, U.S. Pat. No. 4,948,882; Haralambidis et al, Nucleic Acids Research, 15: 4857–4876 (1987); Urdea et at, U.S. Pat. No. 5,093,232; Cruickshank U.S. Pat. No. 5,091,519; Hobbs Jr. et at, U.S. Pat. No. 5,151,507; or the like. Most preferably, nucleotides having pyrimidine moieties are derivatized. In further preference, the 3' terminal nucleotide of the oligonucleotide probe is blocked or rendered incapable of extension by a nucleic acid polymerase. Such blocking is conveniently carried out by the attachment of a phosphate group, e.g. via reagents described by Horn and Urdea, Tetrahedron Lett., 27: 4705 (1986), and commercially available as 5' Phosphate-ON™ from Clontech Laboratories (Palo Alto, Calif.). In a preferred embodiment of the invention, ROX is used as the second fluorophore on the internal reference and the ROX moiety is attached at the 3' postion on the oligonucleotide. The 3' attachment of ROX to oligonucleotides is described in U.S. patent application Ser. No. 08/593,031, which is incorporated by reference.

The separation of the first and second fluorophores within the internal molecules of the invention may vary depending on the nature of the first fluorophore and second fluorophores, the manner in which they are attached, the illumination source, and the like. The first and second fluorophore are preferably close enough so that substantially all, e.g. 90%, of the fluorescence from the first fluorophore is quenched. Typically, for energy transfer-based quenching, the distance between the first and second fluorophores should be within the range of 10–100 angstroms. Preferably, the first and second fluorophores are separated by between about 4 to 10 nucleotides. However, the invention includes embodiments in which the number of nucleotides separating the fluorophores may be greater than 10. Preferably, either the first or second fluorophore is attached to the 5' terminal nucleotide of the oligonucleotide probe. The first or second fluorophore may also be attached to the 3' terminal nucleotide. In other embodiments of the reference molecules of the invention, the first and second fluorophore are attached at internal site on the polynucleotide. The invention also includes embodiments in which the one of the two fluorophores is located at an internal site and the other fluorophore is attached to a terminus of the polynucleotide.

Embodiments of the invention include reagent compositions for use in nucleic acid amplification reactions. The subject compositions comprise the internal reference molecule of the invention and a nucleic acid amplification buffer. The term "nucleic acid amplification buffer" as used herein, refers to a buffered aqueous solution that supports the enzymatic reaction or reactions required for a nucleic acid amplification reaction. The choice of buffer composition will vary in accordance with the particular enzyme selected for catalyzing the nucleic acid amplification reaction of interest. Nucleic acid amplification techniques are well known to persons of ordinary skill in the art of molecular biology. Numerous examples of suitable buffer compositions can be, among other places in the publications such as: PCR: A Practical Approach, Volume 1, eds. M. J. McPherson, P. Quirke, G. R. Taylor, IRL Press (1991); PCR: A Practical Approach, Volume 2, eds. M. J. McPherson, P. Quirke, G. R. Taylor, IRL Press (1995), and PCR Primer, A Laboratory Manual, Eds. C. W. Diffenbach, G. S. Dveksler, Cold Spring Harbor Press (1995). An example of a suitable nucleic acid amplification buffer for Taq DNA polymerase catalyzed amplification reactions is: 10 mM Tris (pH 8.4), 50 mM KCl, 1.5 mM $MgCl_2$, 0.01% gelatin, 0.01% NP40, and 0.01% Tween. Generally, the concentration of internal reference molecule in the subject reagent composition is sufficiently high so as to produce a readily detectable signal from the second fluorophore on the internal reference molecule. Numerous factors affect the choice of internal reference molecule concentration in the subject reagent compositions; such factors include, the amount of fluorescer-quencher probe in the amplification reaction, the sensitivity of the fluorescence detector, the quantum yield of the selected fluorophores, and the like. The subject compositions may further comprise one or more additional compounds required for the nucleic acid amplification reaction of interest, such compounds include: nucleotides, a template for amplification, fluorescer-quencher probes, and the like.

The reagent compositions of the invention may be supplied in a concentrated form or in a form that does not require significant dilution prior to use. The reagent compositions may be used by adding additional compounds required for performing the assay of interest, such compounds include, a thermostable polymerase, nucleotides, a template for amplification, a fluorescer-quencher probes, and the like. After the addition of the necessary additional compounds, the reaction mixture may then be processed accordingly, e.g., thermocycling, so as to produced the desired amplification results.

Fluorescer-quencher probe assays and the subject passive internal reference molecules may be used in conjunction with a variety of nucleic acid amplification systems. Generally, the assays require either the use of a nucleic acid polymerase with exonuclease activity or a population of double stranded DNA which increases during the course of the reaction being monitored. Exemplary amplification schemes that may be employed with the system of the invention include PCR, ligase-based amplification schemes, such as ligase chain reaction (LCR), Q-beta replicase-based amplification schemes, strand displacement amplification (SDA) schemes, such as described by Walker et al, Nucleic Acids Research, 20: 1691–1696 (1992), and the like. A comprehensive description of nucleic acid amplification schemes is provided by Keller and Manak, DNA Probes, Second Edition (Stockton Press, New York, 1993). In preferred embodiments of the invention, the subject internal reference molecules are used in PCR employing fluorescer-quencher probes.

The invention also provides improved methods for measuring the amount of polynucleotide amplification product in a polynucleotide amplification reaction employing fluorescer-quencher probes. The subject methods are particularly advantageous for measuring the amplification product formation in real-time monitored nucleic acid amplification reactions. The subject methods are essentially the same as conventional nucleic acid amplification reactions employing fluorescer-quencher probes, except that the methods of the invention include the step of adding an internal reference of the invention to the amplification reaction. Preferably, the addition step is performed prior to the initiation of the reaction, e.g., before the addition of the DNA polymerase. The fluorescence of the second fluorophore on the internal reference is measured so as to normalize the reaction for such factors that vary from reaction to reaction, e.g., volume or reagent quantities. Thus by examining the ratio of the fluorescent intensities of the fluorescent reporter on a fluorescer-quencher probe and the second fluorophore on the internal reference, the effects of most sources of systematic variability, which would be apparent in the intensities alone, are eliminated.

Fundamental to systems for real time measurement of products from nucleic acid amplifications is the measurement of ratios of fluorescent intensities of a fluorescent reporter on the fluorescer-quencher probe and a second fluorophore present on an internal reference. The fluorescent reporter and the second fluorophore of the internal reference must be spectrally resolvable. That is, their respective emission spectra must be sufficiently non-overlapping so that separate emission peaks are observed in the combined spectrum. Clearly, the system may be generalized to include a plurality of fluorescent reporters, e.g. to monitor the simultaneous amplification of several target nucleic acids in a single reaction, so that a plurality of fluorescent intensity ratios are monitored. Several spectrally resolvable dyes suitable for use in such embodiments are disclosed in Fung et at, U.S. Pat. No. 4,855,225; Menchen et at, U.S. Pat. No. 5,188,934; Bergot et at, International Application PCT/US90/05565; and like references.

In practicing specific embodiments of the invention, consideration must be given to the relationship between the fluorophores on the internal reference and the fluorescent reporter and quencher used on a fluorescent quencher probe assay. The second fluorophore on the internal reference must be different from the quencher on the fluorescer-quencher probe (or probes) used in the same assay. The first fluorophore on the internal reference may be the same or different than the fluorophore used as a reporter on the fluorescer-quencher probe.

Another aspect of the invention is to provide kits for practicing the improved amplification methods of the invention. Kits make the practice of the claimed methods more reproducible and easier to perform. The kits generally comprise two or more reagents required for practicing the subject invention. Kits may supply reagents in pre-measured amounts so as to simplify the performance of the subject methods. Furthermore, kits typically contain detailed instructions for carrying out the methods of the invention. In one embodiment of the kits of the invention, the kit comprises an internal reference of the invention and one or more of the following items fluorescer-quencher probes or a thermostable DNA polymerase suitable for use in fluorescer-quencher probe assays, i.e., having 5'-3' exonuclease activity, such as Taq DNA polymerase. The kits of the invention may further comprise additional reagents that are necessary for performing the subject methods, such reagents include, but are not limited to dNTP mixtures, buffers, molecular size standards, wax beads, and the like.

The real-time detection system includes a sample interface—that is, optical components operationally associated with a closed reaction chamber—which comprises a lens for focusing an excitation beam into the reaction mixture and for collecting the resulting fluorescence and a fiber optic for transmitting both the excitation beam from a light source to the lens and the fluorescent signals from the lens to a detection and analysis means. Preferably, the reaction mixture is contained in a closed reaction chamber to prevent cross-sample contamination, or so-called "carry-over." The lens therefore focuses the excitation beam and collects fluorescence through a portion of a wall of the closed reaction chamber. As mentioned above, the preferred reaction chamber is a tube, e.g. having the geometry and volume of a conventional Eppendorf tube. The tube is closed after the reaction mixture is added by attaching a cap to the open end of the tube. In a preferred embodiment of the sample interface for PCR, the lens directs the excitation beam and collects fluorescence through the cap of the tube, as illustrated in FIG. 1. In the illustrated configuration, a first end fiber optic 2 is held by ferrule 4, housing 6, and plate 10 in a co-axial orientation with lens 8. A second end of fiber optic 2 (not shown) is operationally associated with a light source and detection and analysis means, discussed more fully below. The distance between the end face of fiber optic 2 and lens 8 is determined by several factors, including the numerical aperture of the fiber optic, the geometry of tube 18, the focal length of lens 8, the diameter of lens 8, and the like. Guidance for selecting values for such variables in any particular embodiment is readily found in standard texts on optical design, e.g. Optics Guide 5 (Melles Griot, Irvine, Calif., 1990), or like reference. In the illustrated embodiment, lens 8 has a diameter of 8 mm and is composed of material BK7, available from Edmund Scientific (Barrington,. N.J.). Fiber optic 2 has a numerical aperture of 0.2. Preferably, the design permits maximal transmission of excitation beam 28 to reaction mixture 22. For example, lens 8, numerical aperture of fiber optic 2, and the distance between the end of fiber optic 2 and lens 8 are selected so that the diameter of lens 8 equals or exceeds the diameter of excitation beam 28 where beam 28 impinges on the lens (as illustrated in FIG. 1). Excitation beam 28 is focused through cap 16, void 24, and top surface 26 of reaction mixture 22 to a region approximately 1–3 times the diameter of the fiber optic just below, e.g. 1–3 mm, surface 26. This degree of focusing is not a critical feature of the embodiment; it is a consequence of adapting the sample interface to the geometry and dimensions of a sample holder of a commercially available thermal cycler. In other embodiments, the geometry and dimension may permit a sharper focus into the reaction mixture.

The lens of the invention may have a variety of shapes depending on particular embodiments. For example, the lens may be a sphere, truncated sphere, cylinder, truncated cylinder, oblate spheroid, or truncated oblate spheroid, or the like, and may be composed of any suitably transparent refractive material, such as disclosed by Hlousek, U.S. Pat. No. 5,037,199; Hoppe et at, U.S. Pat. No. 4,747,87; Moring et al, U.S. Pat. No. 5,239,360; Hirschfield, U.S. Pat. No. 4,577,109; or like references.

Fluorescent light generated by excitation beam 28 is collected by lens 8 along approximately the same optical pathway as that defined by excitation beam 28 and focused onto the end of fiber optic 2 for transmission to optical separation and analysis components of the system.

In further preference, the sample interface also includes means for heating the portion of the wall of the reaction chamber used for optical transmission in order to reduce variability due to scatter and/or absorption of the excitation beam and signal from condensation of reaction mixture components. In the embodiment of FIG. 1, the portion of the reaction chamber (tube 18) wall used for optical transmission is cap 16. Accordingly, heating element 12 and heat-conductive platen 14 are employed to heat cap 16. Preferably, heating element 12 comprises resistance heating elements and temperature sensors that permit programmed controlled of the temperature of cap 16. Cap 16 is maintained at a temperature above the condensation points of the components of the reaction mixture. Generally, cap 16 may be maintained at a temperature in the range of 94°–110° C. Preferably, cap 16 is maintained at a temperature in the range of about 102° C. to about 105° C. since the principal solvent in the reaction mixture is usually water. More preferably, cap 16 is maintained at 103° C. Preferably, in embodiments employing thermal cycling, the cap-heating components described above are thermally isolated from heating-conducting component 20 employed to cyclically control the temperature of reaction mixture 22.

Selection of appropriate materials for the components described above is well within the skill of an ordinary mechanical engineer. Exemplary criterion for material selection include (I) degree of thermal expansion, especially for amplification schemes employing thermal cycling, and its affect on the alignment of the optical components, (ii) optical transmission properties in the excitation wavelengths and fluorophore emission wavelengths employed, (iii) chemical inertness of the reaction chamber relative to components of the reaction mixture, (iv) degree to which critical reaction components, e.g. polymerases, target nucleic acids, would tend to adsorb onto chamber walls, (v) minimization of fluorescent materials in the optical pathway, and the like. Typically, tubes containing amplification reaction mixtures are made of polypropylene or like materials.

Figure 2:
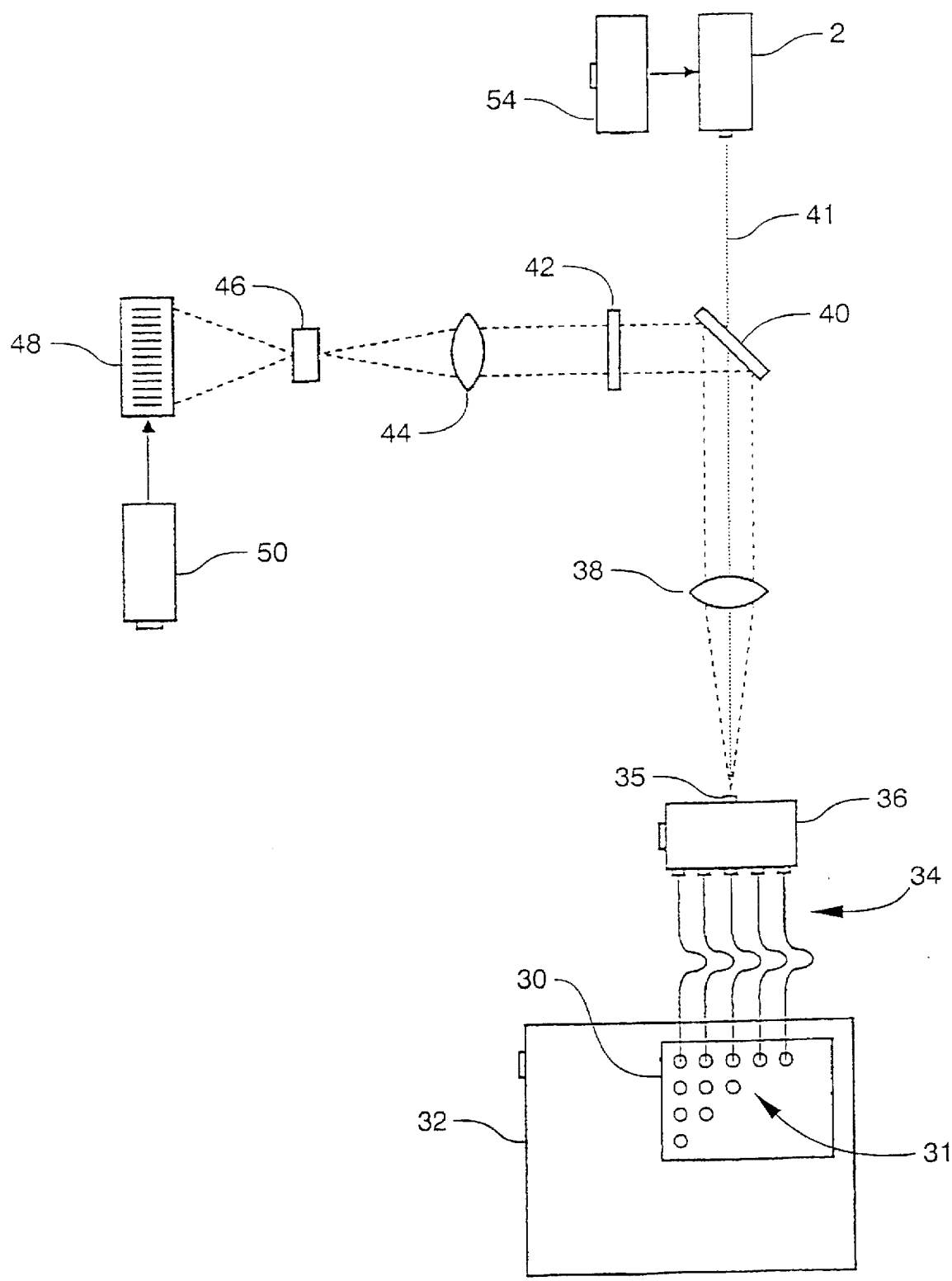
FIG. 2 diagrammatically illustrates a preferred embodiment for simultaneously monitoring a plurality of amplification reactions by sequentially interrogating reactions via a fiber optic multiplexer.

The sample interface shown in FIG. 1 may be employed individually or it may be employed as one of a plurality of identical interfaces in a single instrument, as shown diagrammatically in FIG. 2. In the illustrated embodiment, individual sample interfaces 31, arrayed in holder 30 (which may, for example, be a heating block associated with thermal cycler 32, such as described in Mossa et at, European patent application No. 91311090.4, publ. No. 0488769 A2) are connected by fiber optics 34 to fiber optic multiplexer 36, which selectively permits transmission between individual fiber optics and port 35, e.g under user control via a programmed microprocessor. In a preferred configuration, excitation beam 41, generated by light source 52 and controller 54, passes through beam splitter 40 and is focused onto port 35 by lens 38, where it is sequentially directed by fiber optic multiplexer 36 to each of a predetermined set, or subset, of fiber optics 34. Conversely, a fluorescent signal generated in a reaction chambers is collected by lens 8 and focused onto a fiber optic which, in turn, transmits the signal to a detection and analysis means, possibly via a fiber optic multiplexer. Returning to FIG. 2, a fluorescent signal collected by a sample interface is directed to fiber optic multiplexer 36 where it emerges through port 35 and is collected and collimated by lens 38. Lens 38 directs the fluorescent signal to beam splitter 40 which, in turn, selectively directs the signal through cut-off filter 42, which prevents light from the excitation beam from reaching the signal detection components. Beam splitter 40 may be a conventional dichroic mirror, a fully reflective mirror with an aperture to pass the excitation beam (e.g. as disclosed in U.S. Pat. No. 4,577,109), or like component. After passing through cut-off filter 42, the fluorescent signal is directed by lens 44 to a spectral analyzer which spectrally separates the fluorescent signal and measures the intensities of a plurality of the spectral components of the signal. Typically, a spectral analyzer comprises means for separating the fluorescent signal into its spectral components, such as a prism, diffraction grating, or the like, and an array of photo-detectors, such as a diode array, a charge-coupled device (CCD) system, an array of bandpass filters and photomultiplier tubes, or the like. In the preferred embodiment of FIG. 2, the spectral analyzer comprises diffraction grating 46 (e.g., model CP-140, Jobin-Yvon, N.J.) and CCD array 48 (e.g., model S2135 Princeton Instruments, N.J.), which is linked to CCD controller 50.

An exemplary CCD array suitable for analyzing fluorescent signal from fluorescein and tetramethylrhodamine is partitioned into 21 collection bins which span the 500 nm to 650 nm region of the spectrum. Each bin collects light over a 8.5 nm window. Clearly, many alternative configurations may also be employed. An exemplary application of a CCD array for spectral analysis is described in Karger et at, Nucleic Acids Research, 19: 4955–4962 (1991).

Analyzing the fluorescent signal based on data collected by a spectral analyzer is desirable since components of the signal due to one or more reporter fluorophores (on fluorescer-quencher probes) and the second fluorophore (on the internal reference), from which intensity ratios are calculated, can be analyzed simultaneously and without the introduction of wavelength-specific system variability that might arise, e.g. by misalignment, in a system based on multiple beam splitters, filters, and photomultiplier tubes. Also, a spectral analyzer permits the use of "virtual filters" or the programmed manipulation of data generated from the array of photo-detectors, wherein a plurality of discrete wavelength ranges are sampled—in analogy with physical bandpass filters—under programmable control via an associated microprocessor. This capability permits a high degree of flexibility in the selection of dyes as first and second fluorophores.

Generally, the detection and analysis means may be any detection apparatus to provides a readout that reflect the ratio of intensities of the signals generated by the reporter and internal reference fluorophores. Such apparatus is well know in the art, as exemplified by U.S. Pat. Nos. 4,577,109 and 4,786,886 and references such as The Photonics Design & Applications Handbook, 39th Edition (Laurin Publishing Co., Pittsfield, Mass., 1993).

Preferably, the system of the invention is employed to monitor PCRs, although it may also be employed with a variety of other amplification schemes, such as LCR. Descriptions of and guidance for conducting PCRs is provided in an extensive literature on the subject, e.g. including Innis et al (cited above) and McPherson et al (cited above). Briefly, in a PCR two oligonucleotides are used as primers for a series of synthetic reactions that are catalyzed by a DNA polymerase. These oligonucleotides typically have different sequences and are complementary to sequences that (I) lie on opposite strands of the template, or target, DNA and (ii) flank the segment of DNA that is to be amplified. The target DNA is first denatured by heating in the presence of a large molar excess of each of the two oligonucleotides and the four deoxynucleoside triphosphates (dNTPs). The reaction mixture is then cooled to a temperature that allows the oligonucleotide primers to anneal to their target sequences, after which the annealed primers are extended with DNA polymerase. The cycle of denaturation, annealing, and extension is then repeated many times, typically 25–40 times. Because the products of one round of amplification serve as target nucleic acids for the next, each successive cycle essentially doubles the amount of target DNA, or amplification product.

Clearly, related embodiments of the above may be employed wherein the first fluorophore is attached to an oligonucleotide probe with another non-fluorescent quenching molecule, instead of a second fluorophore. In such embodiments, the second fluorophore could be virtually any spectrally resolvable fluorescent dye that did not interact with the amplification products.

The invention having been described above, may be better understood by reference to the following examples. The examples are offered by way of illustration and should not be construed as a limitation on the invention

EXPERIMENTAL

Real time monitoring of PCR amplification of DNA encoding-actin from various starting concentrations of target DNA A 296 basepair segment of a target DNA encoding human -actin was amplified by PCR from various starting amounts in the range of $5 \times 10^3$ to $1 \times 10^6$ copies of target DNA. The following primers and probe were employed:

5'-TCACCCACACTGTGCCCATCTACGA (SEQ ID NO: 1)
(forward primer)

5'-CAGCGGAACCGCTCATTGCCAATGGT (SEQ ID NO:2)
(reverse primer)

5'-A(FAM)TGCCCT(TMR)CCCCCATGCCATCCTGCGT (SEQ ID NO:3)
(probe)

wherein "FAM" indicates a fluorescein molecule coupled to the oligonucleotide by reacting an NHS-ester group attached to the fluorescein's 6 carbon with a 5'-aminophosphate attached to the 5'-terminal deoxyadenosine of the oligonucleotide in accordance with Fung et at, U.S. Pat. No. 5,212,304; and wherein "TMR" indicates a tetramethylrhodamine molecule coupled to the base moiety of the adjacent thymidine via the amino linking agent disclosed by Urdea et at, U.S. Pat. No. 5,093,232.

PCRs were carried out in 0.2 mL MicroAmp tubes (Perkin-Elmer, Norwalk, Conn.) with the following components: 10 mM Tris-HCl, pH 8.3, 50 mM KCl, 3.5 mM MgCl$_2$, 200M each of the nucleoside triphosphates (with dUTP substituted for dTTP in accordance with U.S. Pat. No. 5,035,996 to prevent carryover contamination), 300 nM each of forward and reverse primers, AmpliTaq™ (Perkin-Elmer, Norwalk, Conn.) at 0.05 U/L. To this mixture was added 5 μL Raji DNA (Applied Biosystems, Foster City, Calif.) at 10 ng/μL, 5 μL probe at 2M, and 1 μL uracil N-glycosylase at 1 unit/μL to bring the reaction volume to 51 μL. Heating and cooling cycles were carried out in a model 9600 Thermal Cycler (Perkin-Elmer, Norwalk, Conn.) fitted with a sample holder cover containing the sample interface components of the invention. The following temperature profile was employed: hold for 2 minutes at 50° C.; hold for 10 minutes at 95° C.; cycle through the following temperatures 40 times: 92° C. for 15 seconds, 54° C. for 15 seconds, 72° C. for 1 minute; then hold at 72° C.

Figure 3:
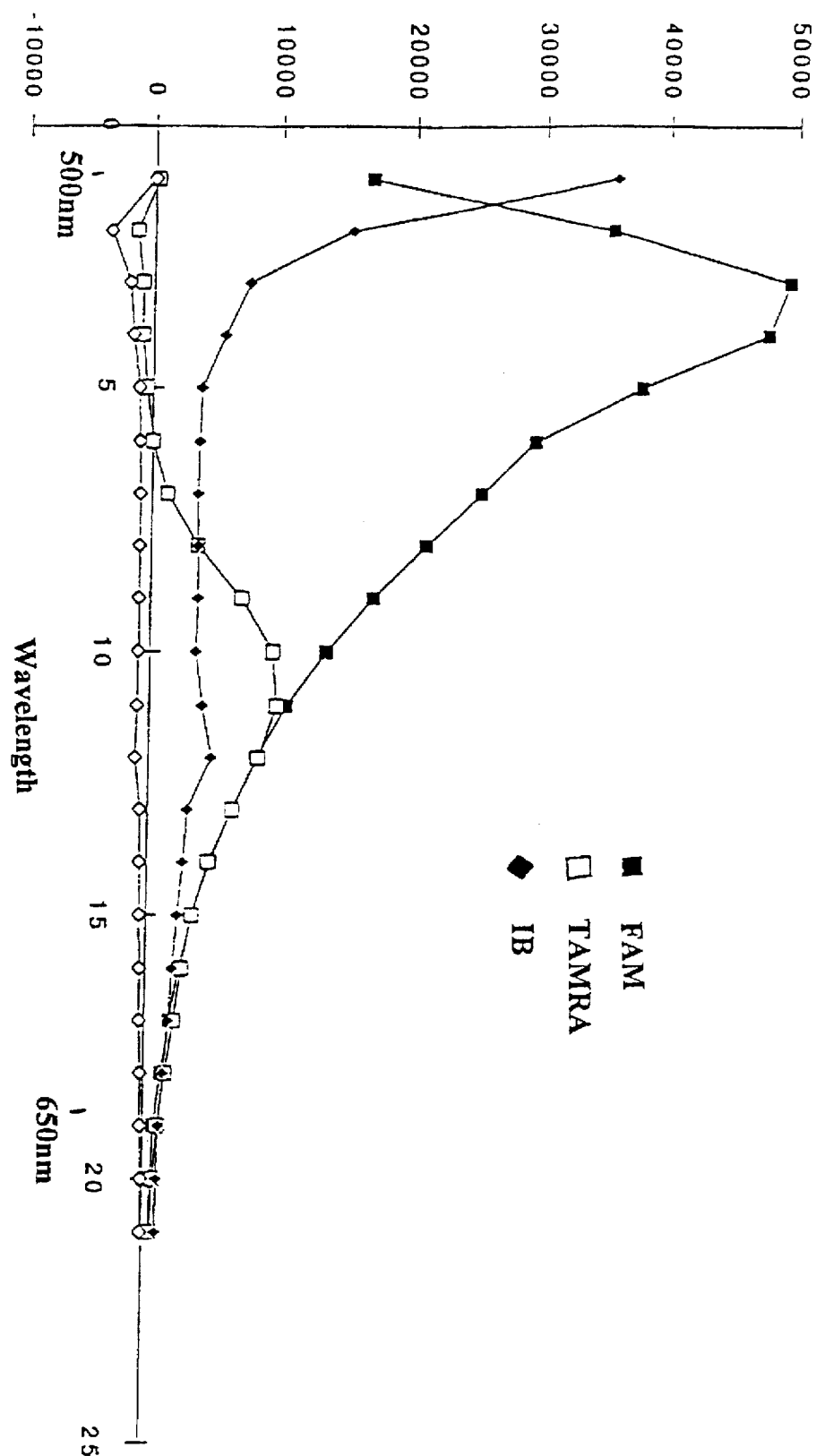
FIG. 3 shows spectrally separated fluorescent intensity data for a tetramethylrhodamine fluorophore, a fluorescein fluorophore, and instrument background registered by a CCD array of the preferred embodiment described below.

FIG. 3 illustrates data showing the emission spectra of the fluorescein and tetramethylrhodamine dyes employed as indicators above and fluorescence due to extraneous sources in the system.

Figure 4:
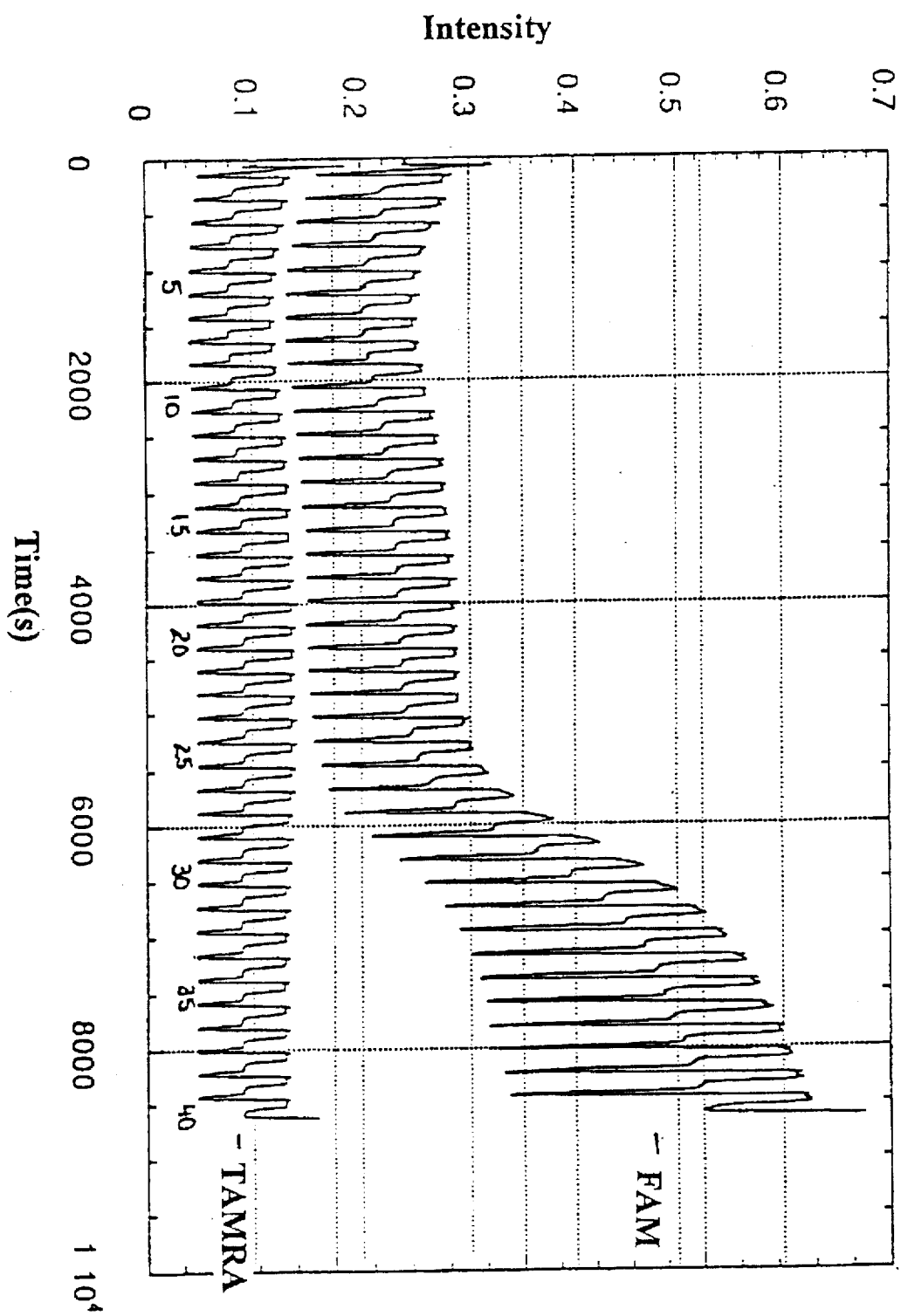
FIG. 4 shows the time dependence of fluorescent signals from a fluorescein dye proportional to the amplification product (first fluorophore) and a tetramethylrhodamine dye employed as a second fluorophore during a typical PCR.
Figure 5:
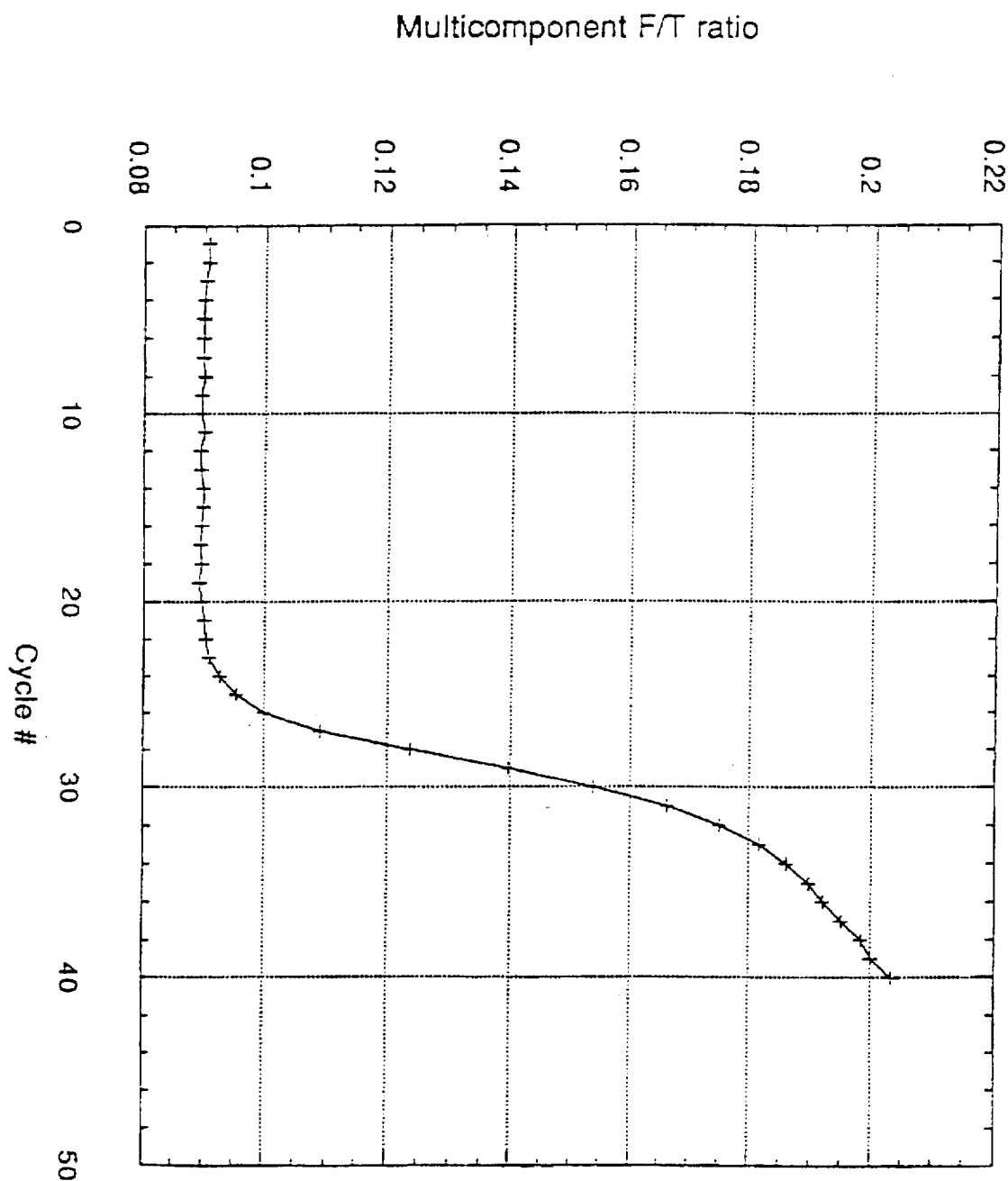
FIG. 5 shows the cycle dependence of the ratio of the intensities of the fluorescein and tetramethylrhodamine dyes from the same PCR whose time dependent data is shown in FIG. 3.

FIG. 4 illustrates data showing fluorescein fluorescent intensity and tetramethylrhodamine fluorescent intensity as a function of cycle number. The high frequency oscillations in intensity reflect the temperature dependence of the fluorescent emission of the two dyes. An increase in base line fluorescence for both dyes between cycles 10 and 28 is a system-based variation. In FIG. 5, which illustrates the ratio of fluorescein-to-tetramethylrhodamine fluorescent intensity from the same data, the system-based variation is eliminated and the RMS of fluctuations in the readout signal, that is, the ratio of fluorescent intensities, is less than 1% of the average magnitude of the measured ratio.

Figure 6:
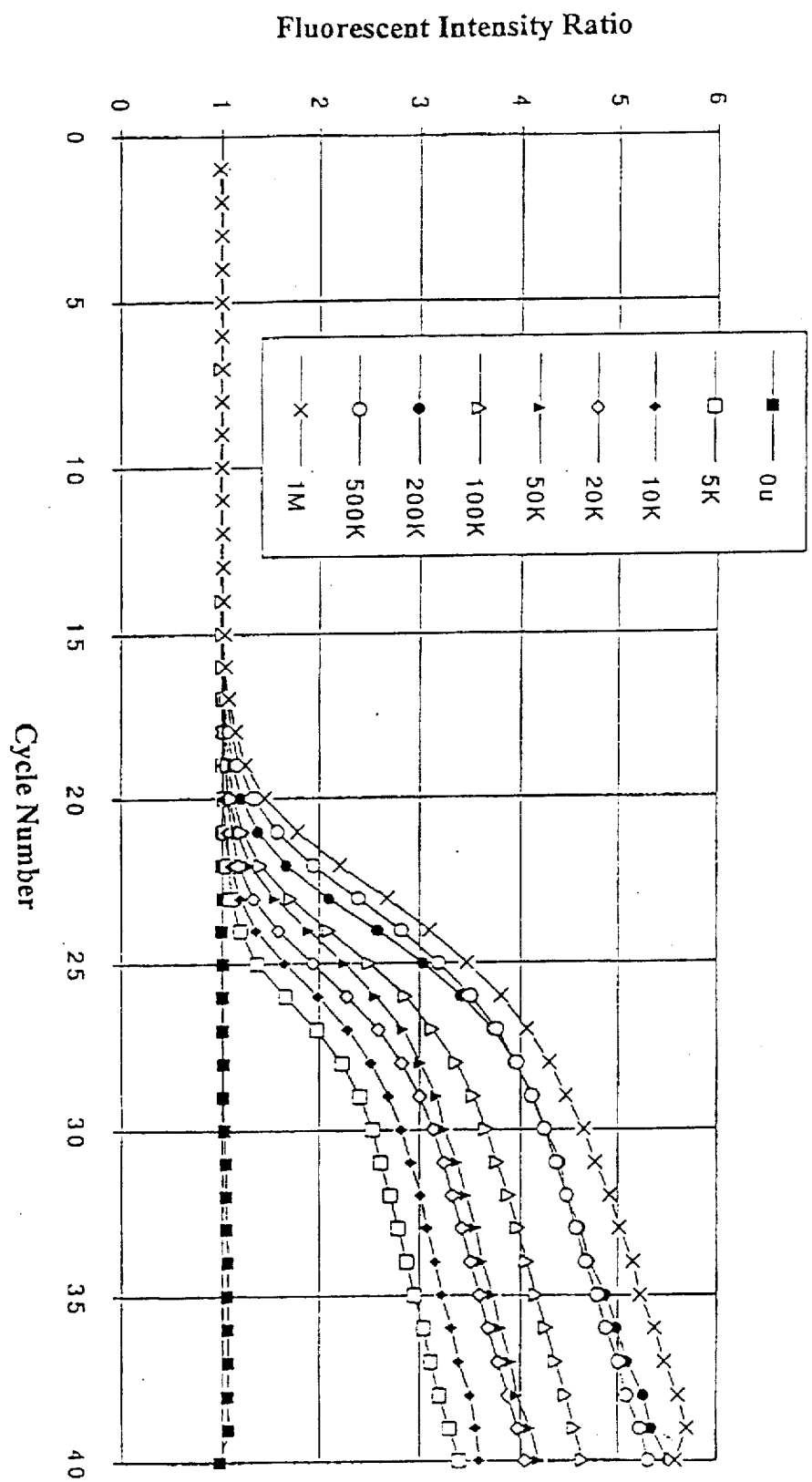
FIG. 6 shows data relating the amount of amplification product to cycle number in separate PCRs having different starting concentrations of the same target nucleic acid.

FIG. 6 illustrates data from PCR of the -actin DNA starting from amounts ranging from 5000 target molecules to 10 target molecules as indicated in the figure.

INCORPORATION BY REFERENCE

This application incorporates all publications and patents referred to herein by reference.

---

What is claimed is:

1. A reagent composition, said composition comprising: a nucleic acid amplification buffer, and an internal reference molecule, said internal reference molecule comprising
a first fluorophore,
a second fluorophore, and
a backbone connector that does not hybridize in a sequence specific manner to a polynucleotide for amplification under nucleic acid amplification conditions, wherein the backbone connector joins the first and second fluorophores so as to permit the transfer of energy from the first fluorophore to the second fluorophore.

2. A composition according to claim 1, wherein the backbone connector is a polynucleotide.

3. A composition according to claim 2, wherein the polynucleotide is 2 to 25 nucleotides in length.

4. A composition according to claim 3, wherein the polynucleotide is (dT)8.

5. A composition according to claim 1 wherein the first fluorophore is selected from the group consisting of fluorescein, 6-carboxyfluorescein, 2',4',5',7',-tetrachloro-4, 7-dichlorofluorescein, 2',7'-dimethoxy-4',5'-6-carboxyrhodamine (JOE), N',N',N',N'-tetramethyl-6-carboxyrhodamine (TAMRA) and 6-carboxy-X-rhodamine (ROX).

6. A composition according to claim 5, wherein the first fluorophore is 6-carboxyfluorescein.

7. A composition according to claim 5 wherein the second fluorophore is selected from the group consisting of fluorescein, 6-carboxyfluorescein, 2',4',5',7',-tetrachloro-4, 7-dichlorofluorescein, 2',7'-dimethoxy-4',5'-6-carboxyrhodamine (JOE), N',N',N',N'-tetramethyl-6-carboxyrhodamine (TAMRA) and 6-carboxy-X-rhodamine (ROX).

8. A composition according to claim 6, wherein the second fluorophore is 6-carboxy-X-rhodamine.

9. In a method of measuring the amount of an amplification product of a polynucleotide for amplification in a nucleic acid reaction wherein the improvement comprises, adding an internal amplification reference molecule to the amplification reaction, said internal reference molecule comprising
a first fluorophore,
a second fluorophore, and
a backbone connector that does not hybridize to the polynucleotide for amplification under nucleic acid amplification conditions,
wherein the backbone connector joins the first and second fluorophores so as to permit the transfer of energy from the first fluorophore to the second fluorophore.

10. A method according to claim 9, wherein the nucleic acid amplification reaction is measured in real-time.

11. A method according to claim 9, wherein the backbone connector is a polynucleotide.

12. A method according to claim 10, wherein the polynucleotide is 2 to 25 nucleotides in length.

13. A method according to claim 12, wherein the polynucleotide is (dT)8.

14. A method according to claim 9 wherein the first fluorophore is selected from the group consisting of fluorescein, 6-carboxyfluorescein, 2',4',5',7',-tetrachloro-4, 7-dichlorofluorescein, 2',7'-dimethoxy-4',5'-6-carboxyrhodamine (JOE), N',N',N',N'-tetramethyl-6-carboxyrhodamine (TAMRA) and 6-carboxy-X-rhodamine (ROX).

15. A method according to claim 14, wherein the first fluorophore is 6-carboxyfluorescein.

16. A method according to claim 14 wherein the second fluorophore is selected from the group consisting of fluorescein, 6-carboxyfluorescein, 2',4',5',7',-tetrachloro-4, 7-dichlorofluorescein, 2',7'-dimethoxy-4',5'-6-carboxyrhodamine (JOE), N',N',N',N'-tetramethyl-6-carboxyrhodamine (TAMRA) and 6-carboxy-X-rhodamine (ROX).

17. A method according to claim 15, wherein the second fluorophore is 6-carboxy-X-rhodamine.

18. A kit for performing nucleic acid amplification reactions, said kit comprising a reagent composition according to claim 1 and one or more reagents selected from the group consisting of a fluorescer-quencher probe and a thermostable DNA polymerase.

19. A kit according to claim 18, wherein said reagent is a fluorescer-quencher probe.

20. A kit according to claim 18, wherein said reagent is a thermostable DNA polymerase.

21. A kit according to claim 20, said kit further comprising a fluorescer-quencher probe.

* * * * *

UNITED STATES PATENT AND TRADEMARK OFFICE
CERTIFICATE OF CORRRECTION

PATENT NO. : 5,736,333
DATED : April 7, 1998
INVENTOR(S) : Livak, et al It is certified that error appears in the above-identified patent and that said Letters Patent is hereby corrected as shown below:

On the title page, under item [56], insert the following:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | EP | 0 | 62 | 3 | 6 | 8 | 2 | 4/28/94 | EP | | | | |
| | | WO | 95/ | 2 | 1 | 2 | 6 | 6 | 8/10/95 | PCT | | | | |
| | | WO | 95/ | 3 | 0 | 1 | 3 | 9 | 11/9/95 | PCT | | | | |
| | | WO | 96/ | 1 | 5 | 2 | 7 | 0 | 5/23/96 | PCT | | | | |
| | | | | | | | | | | | | | | |

Signed and Sealed this

Second Day of March, 1999

*Attest:*

*Attesting Officer*

Q. TODD DICKINSON

*Acting Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

TCACCCACAC TGTGCCCATC TACGA    25

( 2 ) INFORMATION FOR SEQ ID NO: 2:

```
( i ) SEQUENCE CHARACTERISTICS:
      ( A ) LENGTH: 26 nucleotides
      ( B ) TYPE: nucleic acid
      ( C ) STRANDEDNESS: single
      ( D ) TOPOLOGY: linear ( x i ) SEQUENCE DESCRIPTION: SEQ ID NO: 2:

CAGCGGAACC GCTCATTGCC AATGGT                                    2 6

( 2 ) INFORMATION FOR SEQ ID NO: 3:

( i ) SEQUENCE CHARACTERISTICS:
            ( A ) LENGTH: 26 nucleotides
            ( B ) TYPE: nucleic acid
            ( C ) STRANDEDNESS: single
            ( D ) TOPOLOGY: linear ( x i ) SEQUENCE DESCRIPTION: SEQ ID NO: 3:

ATGCCCTCCC CCATGCCATC CTGCGT                                    2 6
```